US 6,592,781 B2

(12) United States Patent
Alink et al.

(10) Patent No.: US 6,592,781 B2
(45) Date of Patent: Jul. 15, 2003

(54) THIAZOLIDINES AND USE THEREOF FOR CORROSION INHIBITION

(75) Inventors: Bernardus Antonius Maria Oude Alink, Sugar Land, TX (US); Benjamin T. Outlaw, Rosenberg, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 10/157,458

(22) Filed: May 29, 2002

(65) Prior Publication Data

US 2002/0139959 A1 Oct. 3, 2002

Related U.S. Application Data

(63) Continuation of application No. 09/455,566, filed on Dec. 6, 1999, now Pat. No. 6,419,857.

(51) Int. Cl.[7] .................. C23F 11/12; C23F 11/14; C23F 11/16; C09K 15/06; C09K 15/12
(52) U.S. Cl. ............... 252/394; 252/395; 252/391; 252/402; 252/405; 252/406; 510/258; 510/401; 548/146; 548/200
(58) Field of Search .................. 252/394, 395, 252/402, 405, 406, 391; 510/258, 401; 548/200, 146

(56) References Cited

U.S. PATENT DOCUMENTS

| 4,443,609 A | 4/1984 | Oude Alink et al. ........ 548/111 |
| 4,477,674 A | 10/1984 | Alink ........................ 548/146 |
| 4,857,537 A | * 8/1989 | Toda et al. .................. 514/365 |
| 4,956,468 A | * 9/1990 | Kerlinger et al. ........... 548/200 |
| 5,197,545 A | 3/1993 | Oude Alink et al. ........ 166/372 |
| 5,202,342 A | * 4/1993 | Morita et al. ................ 514/369 |
| 5,411,976 A | * 5/1995 | Kado et al. .................. 514/365 |
| 5,843,970 A | * 12/1998 | Pershadsingh et al. ....... 514/365 |

FOREIGN PATENT DOCUMENTS

| EP | 03076754 | 4/1991 |
| EP | 10282620 | 10/1998 |

OTHER PUBLICATIONS

6001 Chemical Abstracts, Columbus, Ohio, US vol. 101, No. 18, Oct. 29, 1984, XP–002164682.
6001 Chemical Abstracts, Columbus, Ohio, US vol. 97, No. 9, Aug. 30, 1982, XP–002164683.
XP–002164684 (1991).

* cited by examiner

Primary Examiner—Joseph D. Anthony
(74) Attorney, Agent, or Firm—Madan, Mossman & Sriram, P.C.

(57) ABSTRACT

A novel composition of thiazolidines of the following formula and a method to prepare the same are disclosed. The method involves reacting a dihydrothiazole with a mixture comprising formic acid and an aldehyde. These new thiazolidines are useful as corrosion inhibitors.

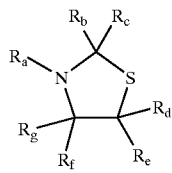

3 Claims, 2 Drawing Sheets

THIAZOLIDINES AND USE THEREOF FOR CORROSION INHIBITION

This application is a continuation of co-pending U.S. application Ser. No. 09/455,566, filed Dec. 6, 1999 now U.S. Pat. No. 6,419,857.

BACKGROUND OF THE INVENTION

1. Field of the Invention

This invention relates generally to novel thiazolidines, the method for making these thiazolidines and the use of the thiazolidines for corrosion inhibition.

2. Background of the Invention

Various sulfur-containing compounds have been used as corrosion inhibitors for many different types of applications. For example, heterocyclic sulfur compounds such as 4-neopentyl-5-t-butyl-1,2-dithiole-3-thione have been used as corrosion inhibitors, particularly in an environment where metal failure through stress cracking is a concern. Another compound, thioglycolic acid, in combination with imidazolines, has been used for North Slope operations in Alaska. While being effective against corrosion, this formulation is quite expensive and has a strong unpleasant odor.

U.S. Pat. No. 5,197,545, assigned to the assignee of this invention, discloses a novel method for volatile inhibition of corrosion and transportation of corrosion inhibitor in a gas lift process in which a gas is pumped into a well to facilitate petroleum production of the well. The corrosion inhibitors used are 2,5-dihydrothiazoles of the following formula:

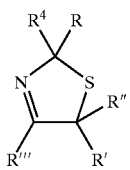

A

R, R', R", R'" and $R^4$ are, independently, H, methyl, ethyl, n-propyl or isopropyl and the total carbon number of these five groups does not exceed about 14. One such compound, 2,5-dihydro-5,5-dimethyl-(1-methylethyl)thiazole, i.e. R=CH(CH$_3$)$_2$, R'=CH$_3$, R"=CH$_3$, R'"=H, and $R^4$=H, is referred to hereinafter as compound A1. These 2,5-dihydrothiazoles are prepared by methods described in U.S. Pat. No. 4,477,674.

While these dihydrothiazoles have good solubilities in hydrocarbons and/or sufficient vapor pressures for both liquid and vapor phase corrosion inhibitions, they do not have high solubilities in systems such as brine, where aqueous corrosion inhibitions are needed. Thioglycolic acid does have sufficient solubility in aqueous systems, but as mentioned before it has a highly unpleasant odor, which makes it less desirable. As a result, in applications where brine is present, there is a need for inhibitors that have low odors and sufficient solubilities in various aqueous systems.

It was unexpectedly discovered that a number of novel N-substituted thiazolidines and their mixtures can be prepared by reacting dihydrothiazoles with a mixture comprising formic acid and formaldehyde under effective conditions.

SUMMARY OF THE INVENTION

The present invention relates to a composition which consists essentially of an N-substituted thiazolidine and mixtures thereof with a structure disclosed herein (structure B below) in the detailed descriptions of the invention section.

It is another object of the present invention to provide a method for preparing such N-thiazolidines by reacting dihydrothiazoles with a mixture comprising formic acid and an aldehyde.

It is a further object of the invention to use the new thiazolidines as corrosion inhibitors.

DETAILED DESCRIPTIONS OF THE INVENTION

Figure 1:
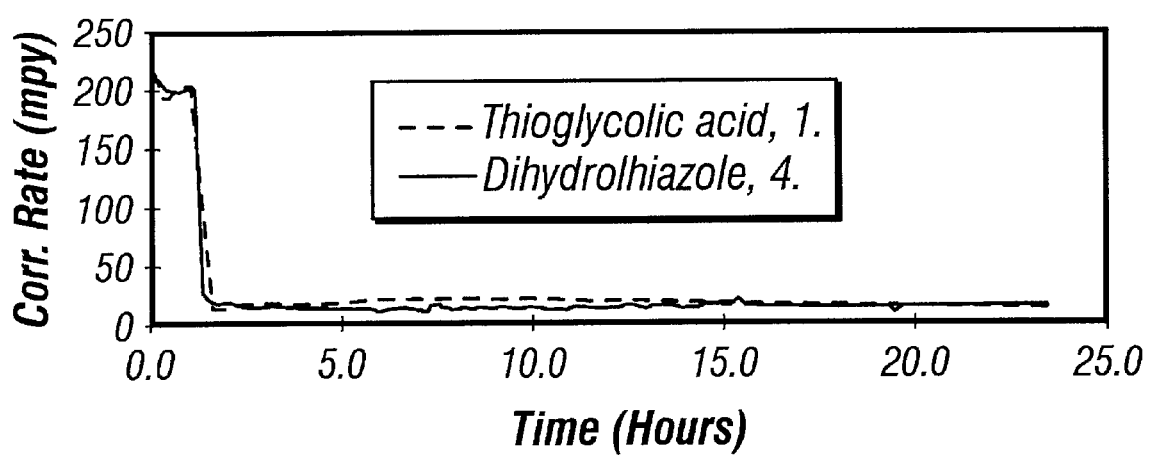
FIG. 1 shows LPR test results of using thioglycolic acid and compound A1 as corrosion inhibitors as a function of time. It can be seen that the corrosion rates decreased substantially shortly after addition of the inhibitors to the system at time of 1.0 hour. See Example 4 for details.

A composition which consists essentially of N-substituted thiazolidines of the following formula and their mixtures is within the embodiment of the present invention.

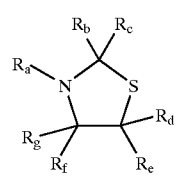

B $R_a$ is selected from the group consisting of $C_1$–$C_5$ linear and branched alkyl groups and formyl group, C(=O)H. CH$_3$, isobutyl, [CH$_2$CH(CH$_3$)$_2$,] and formyl, C(=O)H, are preferred.

$R_b$ is selected from the group consisting of H, $C_1$–$C_5$ linear and branched alkyl groups. H, isopropyl [CH(CH$_3$)$_2$] and isobutyl [CH$_2$CH(CH$_3$)$_2$] are preferred.

$R_c$ is selected from the group consisting of H, $C_1$–$C_5$ linear and branched alkyl groups. H, isopropyl and isobutyl are preferred. H is more preferred when $R_b$ is isopropyl.

$R_d$ is selected from the group consisting of $C_1$–$C_5$ linear and branched alkyl groups. CH$_3$ is preferred.

$R_e$ is selected from the group consisting of $C_1$–$C_5$ linear and branched alkyl groups. CH$_3$ is preferred.

$R_f$ is selected from the group consisting of H, $C_1$–$C_5$ linear and branched alkyl groups. H is preferred.

$R_g$ is selected from the group consisting of H, $C_1$–$C_5$ linear and branched alkyl groups. H is preferred.

The total number of carbon atoms of $R_a$, $R_b$, $R_c$, $R_d$, $R_e$, $R_f$ and $R_g$ is less than about 20.

The following are specific and more preferred combinations of different R groups in the same structure:

I. $R_a$ is $CH_3$, $R_b$ is H, $R_c$ is $CH(CH_3)_2$, $R_d$ is $CH_3$, $R_e$ is $CH_3$, $R_f$ is H and $R_g$ is H.

II. $R_a$ is $CH_2CH(CH_3)_2$, $R_b$ is H, $R_c$ is $CH(CH_3)_2$, $R_d$ is $CH_3$, $R_e$ is $CH_3$, $R_f$ is H and $R_g$ is H.

III. $R_a$ is $CH_2CH(CH_3)_2$, $R_b$ is H, $R_c$ is H, $R_d$ is $CH_3$, $R_e$ is $CH_3$, $R_f$ is H and $R_g$ is H.

IV. $R_a$ is C(=O)H, $R_b$ is H, $R_c$ is $CH(CH_3)_2$, $R_d$ is $CH_3$, $R_e$ is $CH_3$, $R_f$ is H and $R_g$ is H.

V. $R_a$ is $CH_3$, $R_b$ is H, $R_c$ is H, $R_d$ is $CH_3$, $R_e$ is $CH_3$, $R_f$ is H and $R_g$ is H.

VI. Mixtures of I, II, III, IV and V in different amounts.

The term "thiazolidine" used herein means only that the thiazole heterocyclic ring is saturated, i.e. there are no carbon-carbon or carbon-nitrogen double bonds in the ring, or a thiazolidine ring.

Unless specifically referring to a particular pure compound, it is understood that the term "a thiazolidine" or "the thiazolidine" refers to and embodies both individual thiazolidines as well as mixtures which consist essentially of at least one thiazolidine. Similarly, unless specifically referring to a particular pure compound, the term "a dihydrothiazole" or "the dihydrothiazole" refers to and embodies both individual dihydrothiazoles as well as mixtures which consist essentially of at least one dihydrothiazole.

The general method of preparing the N-substituted thiazolidines is carried out by reacting a dihydrothiazole starting material with a mixture comprising formic acid and an aldehyde under conditions effective to produce the product or mixtures of products.

2,5-dihydrothiazoles and their mixtures, which are used as the starting materials for the present invention, can be prepared by the methods described in U.S. Pat. No. 4,477,674. To the extent it discloses such dihydrothiazole preparation methods, this patent is incorporated herein by reference.

In the method of the present invention, a pure dihydrothiazole or a mixture of dihydrothiazoles is mixed with a mixture comprising formic acid and an aldehyde. This could be accomplished by mixing all the components together at the same time, adding part or all of some components to the others over a period of time, or many other possible combinations known to one skilled in the art. Such mixings do not have to be carried out at ambient conditions. They can be performed below, at or above the desired reaction temperature.

The entire reaction mixture is brought to the desired reaction conditions and allowed to proceed over a period of time. The progress of the reaction may be monitored by measuring various physical properties such as pH and the amount of $CO_2$ produced, by on-line or off-line analyses of one or more products, and combinations thereof. The reaction is stopped after a desired reaction time and the products may be separated and purified. The products can be identified with different analytical methods and spectroscopic means such as gas chromatograph (GC), (high pressure) liquid chromatograph (HPLC), infrared (IR), ultraviolet/visible (UV-VIS), nuclear magnetic resonance (NMR), etc. If a mixture of the products is to be used in the applications, the individual products do not need to be isolated as pure products. The concentrations of various components or isomers may still be determined or measured by known analytical methods. In addition to the use for metal corrosion inhibitors, the thiazolidine products of the present invention also may be used as precursors or intermediates for producing pharmaceuticals, therapeutic ingredients, and others.

A reaction temperature higher than the ambient temperature is preferred for the method of preparing thiazolidines. Accordingly, the reaction temperature is preferably in the range of from about 30° C. to about 250° C., more preferably in the range of from about 65° C. to about 150° C. Depending on the composition of all the components present in the reaction system, it may be necessary to use a pressurized reactor in order to carry out the reaction at a higher temperature. In most cases where formaldehyde and formic acid mixtures are used, it is convenient to allow the reaction mixtures to reflux at ambient pressures. The reaction temperatures in such cases are determined by the composition and other properties of the entire reaction mixture.

In addition to atmospheric pressure (~101 kPa) and high pressures (>101 kPa), sub-atmospheric pressures (<~101 kPa) also may be used if desirable. The reaction pressure is in the range of from about 5 kPa to about 500 kPa, preferably from about 60 kPa to about 200 kPa. Even higher pressure may be used, but there is generally no sufficient benefit to warrant its use. One exception is when CO is used as a chemical equivalent of formic acid. (infra) It is preferred to use higher pressure in this case in order to have higher CO concentration in the liquid phase. It is noted that because $CO_2$ is a co-product from the reaction, the reactor pressure may increase as the reaction progresses unless $CO_2$ and/or any other gaseous products or byproducts such as CO are removed as they are produced. For the preferred compositions I, II, III, IV, and V disclosed above, it is more convenient and thus preferable to conduct the experiments at ambient pressures in order to allow carbon dioxide generated by the reaction to escape from the reaction mixture.

Many other variations of the formic acid/aldehyde combination may also be used for the present invention. Different aldehydes or their mixtures may be used. Formaldehyde and isobutyraldehyde are preferred. Formaldehyde in different forms may be used. For instance, pure formaldehyde may be used. Because of its stability problems, aqueous formaldehyde solution can be used. Most commercial aqueous formaldehyde solutions contain about 37 wt % of formaldehyde. Paraformaldehyde may be used as well. Upon heating or hydration, paraformadehyde can generate formaldehyde. Isobutyraldehyde and other aldehydes are typically available from commercial sources in reasonably high purity forms, about >95 wt %.

Similarly, aqueous formic acid solutions may be used as formic acid source. Commercially available formic acid generally contains either about 96 wt % or about 88 wt % formic acid in water. Accordingly, water is generally present in all of the mixtures. Methanol is used commonly to stabilize aqueous formaldehyde. It is therefore present in the mixture when such aqueous formaldehyde solutions are used.

In some cases, formic acid may be eliminated partially or completely from the mixture when formaldehyde is used. Formaldehyde may serve as a source of the formic acid via a disproportionation reaction. Similarly and particularly when the reaction is carried out under sufficiently high reaction pressures in aqueous systems, it may be feasible to use carbon monoxide, CO, with or without hydrogen, to replace part or all of formic acid from the reaction mixture. Formic acid esters, such as methyl formate may also be used to replace formic acid.

The concentrations of the aldehyde and formic acid in the mixture may vary in a preferred range from a mole ratio of from about 0.1 mole of the aldehyde to about 1 mole of formic acid to about 1 mole of the aldehyde to about 0 mole of formic acid. A more preferred range is from about 0.4 mole of the aldehyde to about 1 mole of formic to about 1 mole of the aldehyde to about 0.4 mole of formic acid. There is also water present in this mixture. As noted before, when formaldehyde is used, it may be possible to eliminate formic altogether. The amount of water is in the range of from about 95 wt % to about 5 wt % of the total weight of the mixture.

The method of the present invention allows for use of a wide range of reaction times. The choice of a particular reaction time is largely a function of the reaction mixture composition, reaction temperature, reaction pressure, reaction rate and the desired conversion levels of the starting material, dihydrothiazole. The reaction time is in the range of from about 30 minutes to about 48 hours, preferably from about one hour to about 36 hours. Residence times for continuous, semi-continuous or other flow systems may be determined or calculated by a number of different methods and/or equations known to one skilled in the art.

The reaction can be carried out in various different modes, batch, continuous, semi-continuous and combinations thereof. Reactors such as batch reactor with or without agitation, flow reactor, continuous stirred reactor, pressure reactor or other modifications and combinations of these reactors may be used. If the reaction is carried in a batch reactor, it is preferred to have agitation during the reaction. Regardless of the specific type of reactor or other reaction conditions used, it is preferable for the present invention to remove any $CO_2$ generated continuously.

The compounds and various combinations of the present invention can be used for inhibiting corrosions of metals such as steel, mild steel, carbon steel, cast iron, and others which are exposed to corrosive materials in the presence of water, steam, brine and combinations thereof. The inhibition is effective at a temperature in the range of from about 0° C. to about 250° C., preferably from about 10° C. to about 150° C. Pressure of the system is generally not a critical factor for use of the disclosed compounds.

While one can use very high concentrations of an inhibitor(s) in a particular system, it is preferred to keep the concentration as low as possible to reduce waste, minimize disposal problems, avoid contaminations and lower material cost. The concentration of a particular inhibitor needed for effective inhibition also depends on the metal and the corrosive materials. Generally, an effective concentration of the inhibitor or the inhibitor mixture for the present invention is in the range of from about 0.1 ppm to about 1,000 ppm, preferably from about 0.5 ppm to about 150 ppm, more preferably from about 1 ppm to about 50 ppm.

The products of this invention may be used in combination with other known inhibitors, oxygen scavengers and others. In such cases, the products are formulated with solvents such as alcohols, water, hydrocarbons and mixtures thereof.

For laboratory testing effectiveness of a corrosion inhibitor, a rotating cylinder electrode (RCE) test was carried out with metal coupons. A general procedure as described by the RCE Test Procedures, BPC Test Method Manual #3.29 was followed with some modifications which are discussed further in the example below.

The following examples were carried out to illustrate certain embodiments of the present invention. One having ordinary skill in the art would appreciate the teachings of these examples with respect to the disclosures as well as the claims of the present invention. Moreover, these examples should be read with the drawings to better appreciate the present invention and its advantages.

EXAMPLE 1

A mixture of 42.3 grams of 2,5-dihydro-5,5-dimethyl-(1-methylethyl)thiazole [compound A1, structure A, R=CH$(CH_3)_2$, R'=$CH_3$, R"=$CH_3$, R'''=H, and $R^4$=H], 25 ml of 37 wt % aqueous formaldehyde and 44 grams of 88 wt % formic acid was prepared and refluxed at ambient pressure for 18 hours. The organic layer was separated and the mixture was evaporated under diminished pressure to remove volatiles. This resulted a recovery of 20.2 grams of crude products. After further distillation under reduced pressure, a fraction at a boiling point of 42–58° C. at a pressure of 0.04 mm Hg was collected. Using carbon-13 NMR in $CDCl_3$ solvent with tetramethylsilane (TMS) reference, the product was identified to be 3-N-(1-methylpropyl)-5,5-dimethylthiazolidine [structure B, $R_a$=$CH_2CH(CH_3)_2$, $R_b$=H, $R_c$=CH$(CH_3)_2$, $R_d$=$CH_3$, $R_e$=$CH_3$, $R_f$=H and $R_g$=H]. The NMR chemical shifts in $CDCl_3$, in ppm relative to TMS, of the various carbons of the structure were determined as follows:

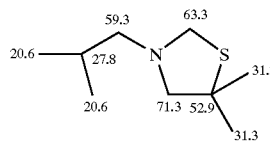

EXAMPLE 2

A mixture of 20.4 grams of 2,5-dihydro-5,5-dimethyl-(1-methylethyl)thiazole [A1, structure A, R=CH$(CH_3)_2$, R'=$CH_3$, R"=$CH_3$, R'''=H, and $R^4$=H], 9.4 grams of isobutyraldehyde, and 18 grams of 88 wt % formic acid was prepared and refluxed at ambient pressure for 21 hours. The organic layer was separated and the mixture was evaporated under diminished pressure to remove volatiles. This resulted in recovery of 20.2 grams of crude products. After further distillation under reduced pressure two products were recovered. Using carbon-13 NMR in $CDCl_3$ solvent with tetramethylsilane (TMS) reference, one product, 11.8 was identified to be 2-isopropyl-3-formyl-5,5-dimethylthiazolidine [structure B, [$R_a$=C(=O)H, $R_b$=H, $R_c$ is CH$(CH_3)_2$, $R_d$=$CH_3$, $R_e$=$CH_3$, $R_f$=J and $R_g$=H]. Another product, 16.2 grams, was identified as 2-(1-methylethyl)-3-N-(1-methylpropyl)-5,5-dimethylthiazolidine [$R_a$=$CH_2$CH$(CH_3)_2$, $R_b$=H, $R_c$=CH$(CH_3)_2$, $R_d$=$CH_3$, $R_e$=$CH_3$, $R_f$=H and $R_g$=H]. The C-13 NMR chemical shifts of the latter structure in $CDCl_3$, in ppm relative to TMS, were determined as follows:

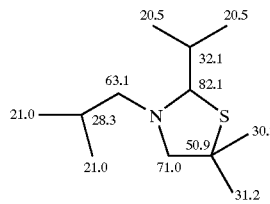

EXAMPLE 3

Example 2 was repeated, except that the individual products were not isolated by further distillation after the organic layer was separated from water present in the reaction product mixture. This mixture was then used for corrosion tests.

EXAMPLE 4

The corrosion test was carried out using mild steel coupons in a Sadlerochit brine/Espersol (80/20, by volume) mixture saturated with high purity $CO_2$ with less than 2 ppm $O_2$ at a pH of 6.3 and a temperature of 160° F. or 71° C. The RCE procedure (supra) was followed except that a step of additional stirring of the brine/oil mixture using a magnetic stirrer at ~1000 rpm, was added to produce a uniform emulsion throughout the test vessel contacting the electrode. The mild steel cylindrical coupons were pre-corroded for one hour before the inhibitor was added to the system. The corrosion rates were monitored during the twenty-four hour testing period by using LPR (linear polarization resistance), weight loss measurements and iron counts.

Figure 2:
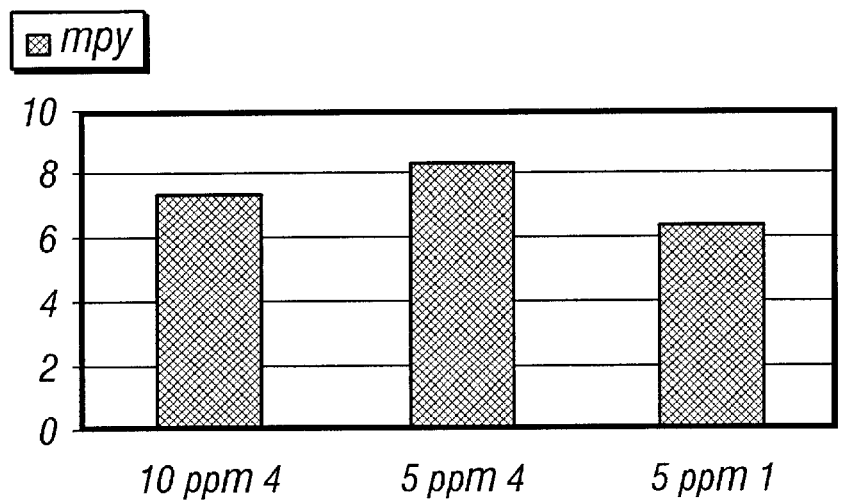
FIG. 2 is a graphical comparison of weight loss of iron coupons in the presence of thioglycolic acid and compound A1. Without any inhibitors, the corrosion rate is about 200 mpy. (mpy=mils per year or $10^{-3}$ inches per year or 2.54× $10^{-3}$ centimeters per year) See FIG. 1 at time of about 0 hour for corrosion rate without inhibitor.

The comparisons of corrosion rates were made at 5 ppm of thioglycolic acid, 5 ppm of A1, and 10 ppm of A1 (see FIGS. 1 and 2). The results showed that shortly after the addition of the corrosion inhibitors (at about the 1.0 hour mark), corrosion rates decreased substantially from the untreated blank system, ~200 mpy, down to less than 10 mpy (mils per year or $10^{-3}$ inches per year or $2.54 \times 10^{-3}$ centimeters per year.) The better the corrosion inhibition by an inhibitor is, the lower the corrosion becomes, i.e. the lower the weight loss.

EXAMPLE 5

The procedure of Example 4 was repeated with a combination VI, which comprises 55% of II, 16% of I, 11% of V and 9% of IV, except that the inhibitor level was set at 10 ppm for the tests.

Figure 3:
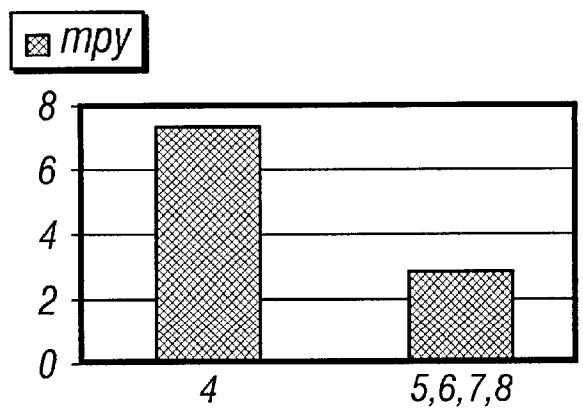
FIG. 3 compares the effectiveness of compound A1 and a mixture of combination VI, which consists essentially of 55 wt % of II, 16 wt % of I, 11 wt % of V and 9 wt % of IV. The mixture of this invention was more effective than A1 because the corrosion rate of the former was over 7 mpy, the latter, less than 4 mpy.

FIG. 3 shows that combination VI of the specific composition of the present invention proved to be more effective that compound A1, a prior art corrosion inhibitor, which is a dihydrothiazole derivative. The corrosion rates were less than 4 mpy (for combination of present invention) and more than 7 mpy (for A1) respectively.

EXAMPLE 6

Figure 4:
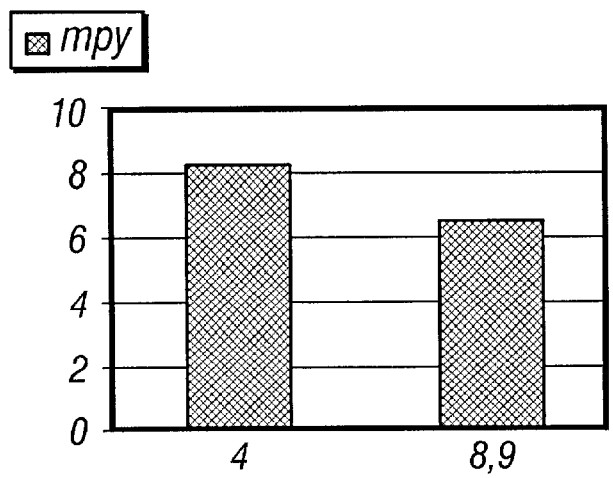
FIG. 4 compares the effectiveness of compound A1 and the product from Example 3 which consists essentially of 42% of combination III and 58% of combination IV. The mixture of the compounds of this invention was again more effective, about 7 mpy corrosion rate against over 8 mpy with A1.

The procedure of Example 4 was repeated with a mixture from Example 3 which consists essentially of 42% of combination III and 58% of combination IV as described heretofore. Both corrosion inhibitors were tested at 5 ppm levels. FIG. 4 shows that a mixture of the compounds of this invention was more effective than A1, about 7 mpy corrosion rate versus over 8 mpy corrosion rate using A1.

The foregoing examples and any preferred embodiments are intended only for illustration purposes to demonstrate the embodied invention. They are not intended to limit the spirit or the scope of the invention, which is described by the entire written disclosure herein and defined by the claims below.

What is claimed is:

1. A method for using a composition as a corrosion inhibitor for a metal surface, the method comprising contacting an effective amount of the composition with the metal surface, wherein the composition consisting essentially of at least one N-substituted thiazolidine having a structure of:

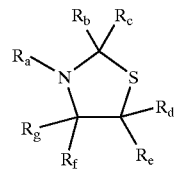

wherein Ra is C(=O)H;

Rb, Rc, Rf and Rg are independently selected from the group consisting of H, C1–C5 linear and branched alkyl groups; and Rd and Re are independently selected from the group consisting of C1–C5 linear and branched alkyl groups; wherein a total number of carbon atoms of Ra, Rb, Rc, Rd, Re, Rf and Rg is less than about 20.

2. The method of claim 1, wherein the effective amount is in the range of from about 1 ppm to about 50 ppm.

3. The method of claim 2, wherein the structure is

Ra is C(=O)H, Rb is H, Rc is CH(CH3)2, Rd is CH3, Re is CH3, Rf is H and Rg is H;

(V) Ra is CH3, Rb is H, Rc is H, Rd is CH3, Re is CH3, Rf is H and Rg is H; and (VI) mixtures thereof.

* * * * *